United States Patent [19]

Sanders et al.

[11] 3,978,090

[45] *Aug. 31, 1976

[54] PROCESS FOR PRODUCTION OF ISOCHROMANS

[75] Inventors: James Milton Sanders, Eatontown; Loren Hall Michael, East Windsor, both of N.J.

[73] Assignee: International Flavors & Fragrances Inc., New York, N.Y.

[ * ] Notice: The portion of the term of this patent subsequent to Oct. 7, 1992, has been disclaimed.

[22] Filed: June 26, 1975

[21] Appl. No.: 590,471

Related U.S. Application Data

[63] Continuation-in-part of Ser. No. 466,068, May 1, 1974, Pat. No. 3,910,964.

[52] U.S. Cl.............................. 260/345.2; 260/613 D
[51] Int. Cl.[2]....................................... C07D 311/02
[58] Field of Search................................. 260/345.2

[56] References Cited
UNITED STATES PATENTS

| | | | |
|---|---|---|---|
| 3,360,530 | 12/1967 | Heeringa et al. | 260/345.2 |
| 3,910,964 | 10/1975 | Sanders et al. | 260/345.2 |

FOREIGN PATENTS OR APPLICATIONS

| | | | |
|---|---|---|---|
| 964,546 | 3/1975 | Canada | 260/648 F |

OTHER PUBLICATIONS

Rieche et al., Ber., 89, 1254 (1956).
Sandler et al., Org. Functional Group Prep., vol. III, pp. 2–5, 59, 60 (1972).

*Primary Examiner*—James O. Thomas, Jr.
*Assistant Examiner*—Nicky Chan
*Attorney, Agent, or Firm*—Arthur L. Liberman; Harold Haidt; Franklin D. Wolffe

[57] ABSTRACT

Process for producing isochromans having the structure:

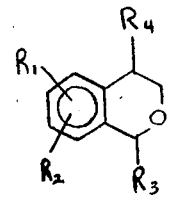

wherein $R_1$ and $R_2$ are each (i) separately selected from the group consisting of hydrogen, lower alkoxyl, lower alkyl, and, (ii) taken together, selected from the group consisting of benzo, cyclopentano, cyclohexano, naphtho, monoalkyl cyclopentano, polyalkyl cyclopentano, monoalkyl cyclohexano and polyalkyl cyclohexano, and $R_3$ and $R_4$ are the same or different and are selected from the group consisting of hydrogen and lower alkyl comprising the steps of intimately admixing:

A. An alkanol having the structure:

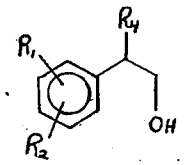

B. An acetal having the structure:

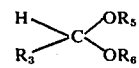

(wherein $R_5$ and $R_6$ are each 2-propyl);
C. a protonic acid selected from the group consisting of p-toluene sulfonic acid and phosphoric acid; and
D. An azeotroping agent selected from the group consisting of n-hexane, cyclohexane, methyl cyclohexane, benzene and toluene;

and simultaneously (i) heating the resulting mixture for a period of time whereby a substantial amount of the isochroman having the above structure is formed while (ii) azeotropically removing water of reaction with the azeotroping agent.

4 Claims, No Drawings

PROCESS FOR PRODUCTION OF ISOCHROMANS

This application is a continuation-in-part of U.S. application for letters patent Ser. No. 466,068 filed on May 1, 1974, now U.S. Pat. No. 3,910,964 issued on Oct. 7, 1975.

BACKGROUND OF THE INVENTION

The production of isochromans has been shown in the art and certain novel isochromans have recently been disclosed with an outstanding musk fragrance. Such isochromans especially adapted for perfumery by virtue of their fragrance properties have been disclosed in Heeringa & Beets U.S. Pat. No. 3,360,530, issued on Dec. 26, 1967.

A number of routes are available for the production of isochromans, such as those set forth in U.S. Pat. No. 3,360,530 and one of the most straightforward of these routes is treatment of a Friedel-Crafts reactant with an alkylene oxide under Friedel-Crafts conditions to form an aryl alkanol. The aryl alkanol is then isolated and thereaffter reacted with formaldehyde to cyclialkylate the alcohol. The efficiency of this multistage process leaves much to be desired because of yield impairment due to the large amount of working required.

U.S. Pat. No. 3,532,719 set forth a process for producing such isochromans which solved a number of the problems of the processes set forth in U.S. Pat. No. 3,360,530. U.S. Pat. No. 3,532,719 provided a more simplified and more economical process for producing isochromans which comprises reacting a Friedel-Crafts reactant with an alkylene oxide in the presence of aluminum chloride to form an aryl alkanol, partially deactivating the aluminum chloride after formation of the aryl alkanol, and cyclialkylating the aryl alkanol with formaldehyde in the presence of the partially deactivated aluminum chloride to form the isochroman. The disadvantage of such procedures for the preparation of isochromans is in the second step wherein chloromethyl methyl ethers may be involved which have been reported to be health hazards and accordingly special precautions are required when handling. The preparation and use of such chloromethyl methyl ethers and the use of aluminum chloride complexes give rise to the release of hydrogen chloride vapors and formation of aqueous hydrogen chloride solutions requires the use of more expensive glass lined vessels due to the more corrosive mixtures in the reaction.

Steyn and Holzapfel, *Tetrahedron*, 23, 4449 (1967), reports the reaction of a halo aryl alkanol with chloromethyl methyl ether and zinc chloride to give an isochroman according to the following reaction:

Meyer and Turner, *Tetrahedron*, 27, 2609, (1971), reports the reaction of a methoxy aryl alkanol with sodium hydride and chloromethyl methyl ether to give a methoxy aryl alkanol methyl ether. Subsequent treatment of the methoxy aryl alkanol methyl ether with toluenesulfonic acid is indicated to yield isochromans according to the following reaction:

THE INVENTION

The present invention provides a simplified, economical process for producing isochromans from substituted aryl alkanols without the involvement of hydrogen chloride or corrosive halide salts or chloromethyl methyl ethers. More specifically, the present invention provides a process for preparing an isochroman having the structure:

wherein $R_1$ and $R_2$ are each (i) separately selected from the group consisting of hydrogen, lower alkoxyl, lower alkyl, and (ii) taken together selected from the group consisting of benzo, cyclopentano, cyclohexano, naphtho, monoalkyl cyclopentano, polyalkyl cyclopentano, monoalkyl cyclohexano and polyalkyl cyclohexano, and $R_3$ and $R_4$ are the same or different and are selected from the group consisting of hydrogen and lower alkyl comprising the steps of admixing:

A. An alkanol having the structure:

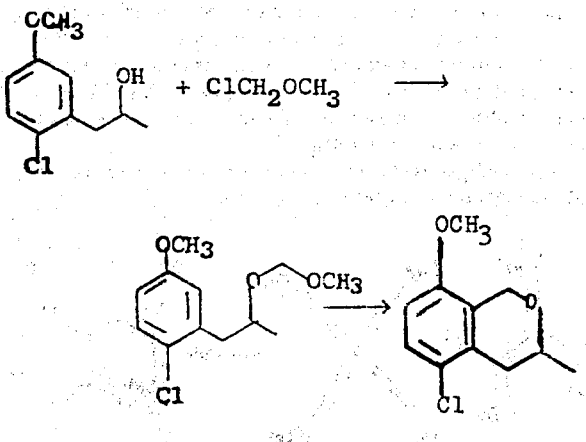

B. An acetal having the structure:

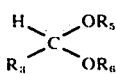

(wherein $R_5$ and $R_6$ are each 2-propyl);
C. A protonic acid selected from the group consisting of p-toluene sulfonic acid and phosphoric acid; and
D. An azeotroping agent selected from the group consisting of n-hexane, cyclohexane, methyl cyclohexane, benzene and toluene;

and simultaneously (i) heating the resulting mixture for a period of time whereby a substantial amount of the isochroman having the above structure is formed while (ii) azeotropically removing water of reaction with the azeotroping agent.

We now have found that the secondary alcohol, isopropanol, can be used as the carrier alcohol if an azeotroping agent such as hexane is also added. The azeotroping agent is needed to permit the removal of the water formed during the reaction by azeotropic distillation and to cause the distillate to separate into an aqueous phase and an organic phase, which can be returned to the reactor. In the absence of the added azeotroping agent the water and isopropanol distill over as a single phase. Although the reaction could be carried out without an added azeotroping agent if fresh isopropanol were added to replace that distilled out with the water, this would require the use of considerably more isopropanol than the procedure using hexane and, in addition, if the isopropanol were to be re-used in the process, it would still have to be dried in some manner.

The modifications now introduced relative to the parent patent application of the instant continuation-in-part application are as follows:
1. A secondary alcohol, isopropanol, can advantageously be used in place of primary alcohols;
2. An azeotroping agent such as hexane is added in order to permit separation of the aqueous and organic layers of the distillate. The azeotroping agent should be inert to the reaction conditions and efficiently separate isopropanol from water. In addition to hexane, other materials which could be used in this way are cyclohexane, benzene, toluene and methylcyclohexane. The amount of hexane or other azeotroping agent used is 5% to 50% based on the weight of aryl alkanol charged. The preferred range is 5% to 15%.

This modified process using isopropanol and an azeotroping agent (e.g. n-hexane) has the following advantages over the process using n-hexanol:
1. Isopropanol is less expensive than n-hexanol.
2. A lower weight of isopropanol than n-hexanol is needed to give the same number of moles of carrier alcohol, thereby permitting an increased throughput in the reaction; and
3. A lower reaction temperature is required: 80°–95°C using isopropanol compared to 140°C using n-hexanol.

The above-mentioned acetal can be formed prior to use in the reaction or, it may be formed in situ.

The acid concentration in the reaction may be in the range of 1% – 100% weight/weight based on the total weight of other reagents charged. The preferred range depends upon the acid used. Two preferred acids which may be used are phosphoric acid and p-toluene sulfonic acid. When 85% phosphoric acid is used, the preferred concentration is 1% to 50% weight/weight based on the total of other reagents used.

Where the acetal is formed in situ, it is formed by reaction of an aldehyde and 2-propanol. The concentration of the aldehyde may be in the range of 0.1 mole up to 100 moles or more per mole of aryl alkanol. The preferred range is 1 – 5 moles of aldehyde per mole of aryl alkanol. The alcohol used to react with the aldehyde to form the acetal may be used in a concentration of 0.1 – 100 moles per mole of the aryl alkanol. If the aldehyde is taken in less than 0.5 moles per mole of aryl alkanol, it is probably not necessary to use more than 0.1 moles of isopropanol per mole of aryl alkanol.

When the aldehyde is taken in an amount greater than 0.5 mole per mole of aryl alkanol, the isopropanol should be taken in an amount at least equal to twice the difference between the number of moles of aldehyde and half the number of moles of aryl alkanol whereby it is insured that all of the aldehyde is converted into an acetal to prevent self condensation of the aldehyde under acidic reaction conditions. It is preferred to use an excess of isopropanol over that required for complete conversion of the aldehyde to the acetal. If desired, the isopropanol can also be used as a solvent for the reaction.

The reaction temperature may be in the range of 0°C up to 200°C, with the range of 80°–95°C being particularly preferred.

The reaction pressure may be equal to, above or below atmospheric pressure so long as the necessary reaction temperature is obtained to give a reasonable rate of conversion to the isochroman. By suitable choice of reagents it is possible to carry out the reaction smoothly at atmospheric pressure, thereby avoiding the necessity of using more expensive pressure or vacuum equipment.

It must be emphasized that the reaction mixture using phosphoric acid or p-toluene sulfonic acid is significantly less corrosive than the prior art processes which give aqueous hydrogen chloride and release hydrogen chloride vapors. This permits the use of less expensive steel reaction vessels rather than the more expensive glass lined vessels required for the more corrosive mixture. Furthermore, in the instant process no chloromethyl methyl ethers are involved either as reagents or intermediates. This class of compound has been reported to be a severe health hazard requiring special precautions when handling.

According to the process of our invention the reactions can be represented as follows:

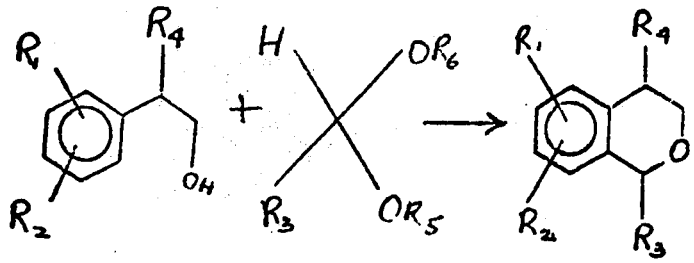

The acetal reactant may be formed ahead of time or in situ according to the following reaction:

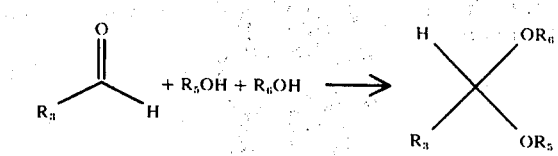

Examples of aryl alkanols that may be used in the reaction of our invention are as follows:
Phenyl ethyl alcohol
2-(1',1',2',3',3'-pentamethylindan-5'-yl)-1-propanol [prepared according to the process of Example XV (b) of U.S. Pat. No. 3,360,530]
1-(2-hydroxyethyl)-3,5-diethylbenzene
1-(2-hydroxyethyl)-2-methoxy-4-methylbenzene
2-(1',1',2',3',3'-pentamethylindan-5'-yl)-ethanol
2-phenyl-1-propanol
2-(1',1',2',3',3'-pentamethylindan-5'-yl)-pentanol-1

Examples of aldehydes useful in forming the acetal reactants of the process of our invention are as follows:
Formaldehyde
Acetaldehyde
Propionaldehyde Easily decomposable precursors of these aldehydes may be used in place of the aldehydes per se, for example paraformaldehyde (to produce formaldehyde) and paraldehyde (to product acetaldehyde).

In the above reactions, $R_1$ and $R_2$ are each (i) separately selected from the group consisting of hydrogen, lower alkoxyl, lower alkyl, and, (ii) taken together, selected from the group consisting of benzo, cyclopentano, cyclohexano, naphtho, monoalkyl cyclopentano, polyalkyl cyclohexano; and $R_3$ and $R_4$ are the same or different and are selected from the group consisting of hydrogen and lower alkyl. $R_5$ and $R_6$ are each isopropyl. A specific example of one of the reactions of the process of our invention is the reaction of the 2-propyl alcohol acetal of formaldehyde with 2-(1',1',2',3',3'-pentamethylindan-5'-yl)-propanol-1 which yields 6-oxa-1,1,2,3,3,8-hexamethyl-2,3,5,6,7,8,-hexahydro-1H-benz [f] indene as follows:

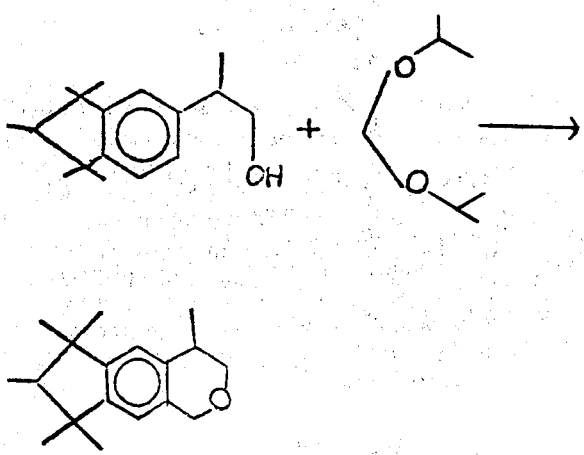

Another example of the process of our invention is the formation 2-oxa-4,5,5,8,8-pentamethyl-1,2,3,4,5,6,7,8-octahydroanthracene as follows:

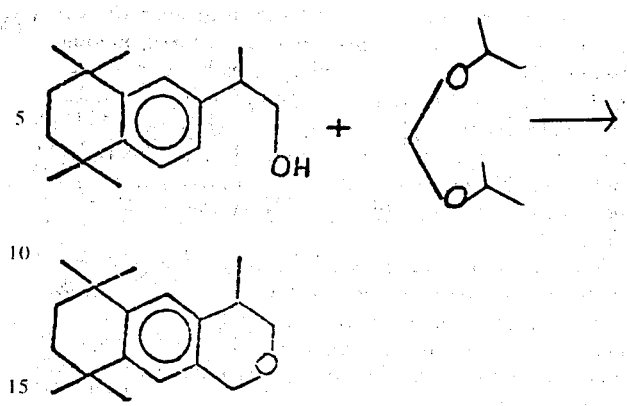

The same reaction whereby the acetal reactant is formed in situ is as follows:

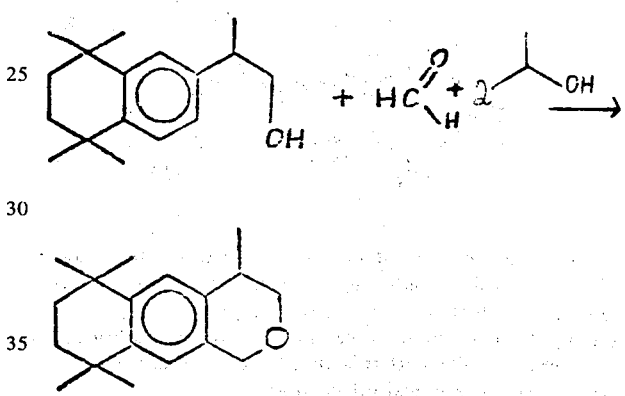

The same material may also be prepared using another reaction sequence which sequence includes a reaction which is an embodiment of our invention, thus:

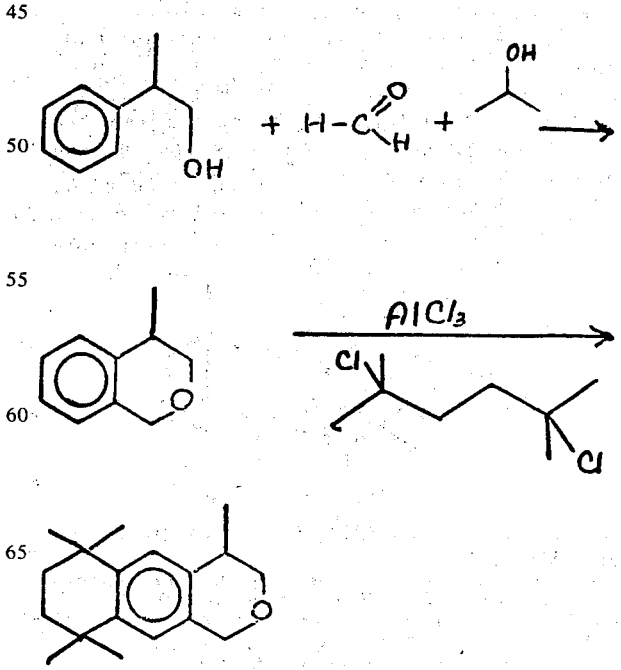

After the reaction of our invention to form the isochroman, the reaction mass is neutralized with aqueous base such as aqueous sodium hydroxide or potassium hydroxide solution and the washed mixture is then treated by conventional techniques such as distillation, extraction, preparative chromaography, and the like, to obtain highly purified isochroman. Fractional distillation is a preferred method of recovering the isochroman.

The following examples are given to illustrate embodiments of the invention as it is presently preferred to practice it. It will be understood that these examples are illustrative, and the invention is not to be considered as restricted thereto except as indicated in the appended claims.

EXAMPLE I

To a 5-liter flask is charged 1935 g of 2-(1',1',2',3',-3'-pentamethylindan-5-yl)-1-propanol [prepared according to the process of Example XV (b) of U.S. Pat. No. 3,360,530] having the structure:

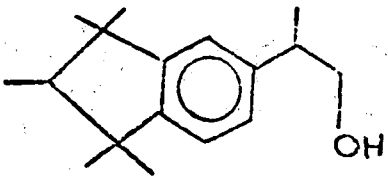

233 g of paraformaldehyde, 370 g of isopropanol, and 127 g of p-toluenesulfonic acid. The stirred mixture is heated to reflux (94°–95°C) over a period of approximately 4 hours and is stirred at reflux for an additional 10 hours. Analysis at this point indicates incomplete conversion to the desired product.

N-hexane (200g) is added and the mixture is stirred at reflux while removing the water by azeotropic distillation. The reflux temperature rises from 81°C to 94°C over a period of 8 hours. After an additional 3 hours a total of 213 ml of aqueous solution is azeotroped out and analysis of the reaction mixture indicates essentially complete conversion to the desired product. The bulk of the isopropanol is recovered by distillation to 120°C pot temperature and the residual material in the reactor is washed at 80°C with 515 g of 20% sodium hydroxide solution. After adding 70 g Primol (See Note 1), 70 g 20% NaOCH$_3$ in CH$_3$OH and 3 g Ionol (See Note 2) distillation of the washed organic material gives an 85% yield of 6-oxa-1,1,2,3,3,8-hexamethyl-2,3,5,6,7,8-hexamethyl-2,3,5,6,7,8-hexahydro-1H-benz [f] indene having the structure:

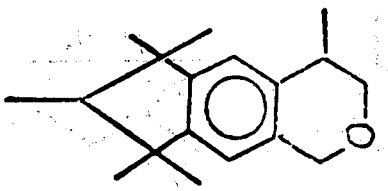

The structure is confirmed by GLC, mass spectral, IR and NMR analyses.

Note 1: Primol is a registered trademark identifying a hydrocarbon mineral oil produced by Exxon Corp. of Linden, N.J.
Note 2: Ionol is a registered trademark identifying the compound 2,6-di-t-butyl-4-methyl phenol.

What is claimed is:
1. In the process for producing isochromans having the structure:

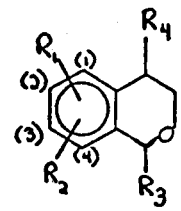

wherein R$_1$ and R$_2$ are each (i) separately, selected from the group consisting of hydrogen, lower alkoxyl, and lower alkyl, and (ii) taken together, when R$_1$ and R$_2$ are located at the "2" and "3" positions of the benzene ring, selected from the group consisting of benzo, cyclopentano, cyclohexano, naphtho, mono-lower alkyl cyclopentano, poly-lower alkyl cyclopentano, mono-lower alkyl cyclohexano and poly-lower alkyl cyclohexano, and R$_3$ and R$_4$ are the same or different and are selected from the group consisting of hydrogen and lower alkyl, comprising the steps of intimately admixing:

A. An aryl alkanol having the structure:

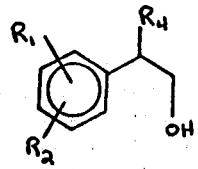

B. A methylenating-cyclizing agent capable of introducing the moiety:

between the oxygen atom and the number "5" carbon atom of the structure:

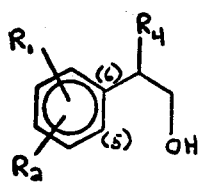

C. A catalyst for the reaction between said aryl alkanol and said methylenating-cyclizing agent
and heating the resulting mixture for a period of time whereby a substantial amount of (i) the isochroman having the above structure is formed and (ii) water of reaction is formed; the improvement consisting of:
1. The methylenating-cyclizing agent being an acetal having the structure:

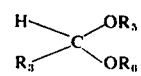

wherein R$_5$ and R$_6$ are each 2-propyl;
2. The catalyst being a protonic acid selected from the group consisting of p-toluene sulfonic acid and phosphoric acid;

3. The reaction mass not containing at any time during or subsequent to the reaction any hydrogen chloride or corrosive halide salts or chloromethyl methyl ethers;
4. The reaction temperature being in the range of from 80° up to 95°C;
5. The acid concentration being fromm 1 up to 100% by weight based on the weight of the remainder of the reaction mass;
6. The ratio of acetal to aryl alkanol being at least 0.1:1; and
7. The reaction taking place in the presence of an azeotroping agent which effects azeotropic removal of said water of reaction, said azeotroping agent being selected from the group consisting of n-hexane, cyclohexane, methyl cyclohexane, benzene and toluene said acetal being formed in situ by admixing an aldehyde of the structure:

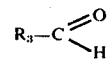

with 2-propanol wherein $R_3$ is hydrogen or lower alkyl.

2. The process of claim 1 wherein $R_3$ is hydrogen.
3. The process of claim 1 wherein $R_3$ is methyl.
4. The process of claim 3 wherein the azeotroping agent is n-hexane.

* * * * *